(12) United States Patent
Humphries

(10) Patent No.: US 7,046,259 B2
(45) Date of Patent: May 16, 2006

(54) METHOD AND SYSTEM FOR PRESENTING DIFFERENT VIEWS TO PASSENGERS IN A MOVING VEHICLE

(75) Inventor: Orin L. Humphries, Lynnwood, WA (US)

(73) Assignee: The Boeing Company, Seattle, WA (US)

( * ) Notice: Subject to any disclaimer, the term of this patent is extended or adjusted under 35 U.S.C. 154(b) by 171 days.

(21) Appl. No.: 10/427,429

(22) Filed: Apr. 30, 2003

(65) Prior Publication Data

US 2004/0217978 A1 Nov. 4, 2004

(51) Int. Cl.
*G09G 5/00* (2006.01)

(52) U.S. Cl. .......................... 345/649; 345/656; 348/148
(58) Field of Classification Search ................. 345/649, 345/656, 659; 348/148, 149, 117, 118, 208.3; 701/1, 3
See application file for complete search history.

(56) References Cited

U.S. PATENT DOCUMENTS

| | | | |
|---|---|---|---|
| 2,861,806 A | 11/1958 | Disney | |
| 4,937,751 A | 6/1990 | Nimura et al. | |
| 5,004,225 A | 4/1991 | Krukovsky | |
| 5,031,860 A | 7/1991 | Ruiz et al. | |
| 5,253,051 A | 10/1993 | McManigal | |
| 5,316,480 A | 5/1994 | Ellsworth | |
| 5,499,120 A | 3/1996 | Hansen | |
| 5,610,822 A | 3/1997 | Murphy | |
| 6,102,332 A | 8/2000 | Haxton et al. | |
| 6,497,649 B1 | 7/2002 | Parker et al. | |
| 6,443,913 B1 | 9/2002 | Kania | |
| 6,538,622 B1 | 3/2003 | Kojima et al. | |
| 6,661,353 B1 | 12/2003 | Gopen | |
| 6,693,518 B1 | 2/2004 | Kumata et al. | |
| 6,704,653 B1 * | 3/2004 | Kuriya et al. ............... 348/148 |
| 6,714,141 B1 | 3/2004 | Kennedy | |
| 6,886,225 B1 | 5/2005 | Pasquetto | |
| 2003/0021445 A1 * | 1/2003 | Larice et al. ............... 348/148 |
| 2003/0078713 A1 | 4/2003 | Tanaka | |
| 2003/0083790 A1 | 5/2003 | Hattori | |
| 2003/0107499 A1 | 6/2003 | Lepere et al. | |
| 2002/0123829 A1 | 9/2003 | Kuriya | |
| 2003/0179109 A1 | 9/2003 | Chamas | |
| 2004/0051634 A1 * | 3/2004 | Schofield et al. ........... 348/148 |
| 2002/0183929 A1 | 9/2004 | Tsuji et al. | |
| 2004/0189831 A1 | 9/2004 | Shibatani | |
| 2004/0217976 A1 | 11/2004 | Sanford | |
| 2004/0217978 A1 | 11/2004 | Humphries | |

OTHER PUBLICATIONS

Kaiser, Mary K. et al., "Dynamic Eye–Point Displays," (2 pages) http://vision.arc.nasa.gov/HST/Brief/Vision.S.T./Dynamic.E.html [Accessed Dec. 4, 2002].

O'Gara Aviation Company, "0'Gara Aviation Company is Proud to Offer For Sale: 1974 Dassault Breguet Falcon 20f–5BR, Ser. No. 313, N184TS," http://www.ogara-jets.com/aircraft for sale/Falcon 20F 313/PHOTOS.HTM, [Accessed Oct. 4, 2005 ].

* cited by examiner

*Primary Examiner*—Matthew Luu
(74) *Attorney, Agent, or Firm*—Perkins Coie LLP

(57) ABSTRACT

Systems and methods for presenting images in a vehicle as the vehicle rotates about a rotation axis are disclosed. In one embodiment, the system includes a signal receiving portion that receives a first signal corresponding to an image of a first view from a position located a first distance from the rotation axis. A signal processing portion directs to a signal display portion located a second distance from the rotation axis, a time varying second signal that represents a second view. The second view can be a portion of the first view and can occupy an area less than the area occupied by the first view. The location of the second area relative to the first area can be selected based at least on an amount by which the first and second distances differ.

22 Claims, 8 Drawing Sheets

US 7,046,259 B2

METHOD AND SYSTEM FOR PRESENTING DIFFERENT VIEWS TO PASSENGERS IN A MOVING VEHICLE

CROSS-REFERENCE TO RELATED APPLICATIONS

The present application is related to and incorporates by reference the following U.S. Patent Applications, filed simultaneously herewith:

1. U.S. application Ser. No. 10/427,405 entitled METHOD AND SYSTEM FOR PRESENTING MOVING SIMULATED IMAGES IN A MOVING VEHICLE; and 2. U.S. application Ser. No. 10/427,677 entitled METHOD AND SYSTEM FOR PRESENTING AN IMAGE OF AN EXTERNAL VIEW IN A MOVING VEHICLE.

TECHNICAL FIELD

The present invention relates to methods and systems for presenting different views of a scene external to a moving vehicle, for example, presenting different images of a region external to an aircraft to passengers seated at different positions within the aircraft.

BACKGROUND

Some vehicles provide limited visual access to the region exterior to the vehicle. For example, some trucks and buses provide limited visual access to the region directly behind the vehicle. One method for overcoming this drawback is to provide the vehicle with an aft-pointing camera that is connected to a display panel inside the vehicle. The display panel can accordingly present to the vehicle driver an image of what the driver would see if he or she were able to look through the rear of the vehicle. This system can therefore aid the driver as the driver backs up the vehicle or engages in other maneuvers that benefit from an aft-facing view. Another existing system includes a passenger aircraft seat-back display that schematically portrays the aircraft superimposed on a map of the terrain the aircraft overflies. However, the foregoing systems can be limited because they present the same image to one or more viewers. Accordingly, the foregoing systems may not be adequate to provide multiple viewers at different positions within the vehicle with an accurate view of the external world outside the vehicle as the vehicle moves.

SUMMARY

The present invention is directed toward methods and systems for presenting an image in a vehicle as the vehicle rotates about a rotation axis. A system in accordance with one aspect of the invention includes a signal receiving portion configured to receive a first signal corresponding to an image of a first view from a position located a first distance from the rotation axis. The first view can encompass a first viewing area. The system can further include a signal processing portion configured to direct to a display portion located a second distance from the rotation axis a time-varying second signal. The time-varying second signal can represent a second view, with the second view being a portion of the first view and occupying a second area less than the first area. The location of the second area relative to the first area can be selected based at least in part on an amount by which the first and second distances differ. Accordingly, passengers within the vehicle located at different distances from the rotation axis can receive images that provide visual cues that are consistent with the motion the passengers feel.

A system in accordance with another embodiment of the invention can include a first display portion positioned within the vehicle at a first distance from the rotation axis, and a second display portion positioned within the vehicle at a second distance from the rotation axis, with the second distance being different than the first distance. A first image source can be positioned at a third distance from the rotation axis and can be operatively coupled to the first display portion to transmit to the first display portion a first signal corresponding to a first image of a view external to the vehicle. A second image source can be positioned a fourth distance from the rotation axis and can be operatively coupled to the second display portion to transmit to the second display portion a second signal corresponding to a second image of a view external to the vehicle. The fourth distance can be different than the third distance and the second distance can be different than the first distance. Accordingly, the multiple image sources can provide occupants of the vehicle with views consistent with the motion they feel, even if they are positioned at different distances from the rotation axis of the vehicle.

A method in accordance with another aspect of the invention includes (while the vehicle rotates about a rotation axis) receiving a first signal corresponding to an image of a first view from a position located a first distance from the rotation axis. The first view can encompass a first viewing area. The method can further include directing a second signal to a display portion of the vehicle, with the display portion being positioned a second distance from the rotation axis. When the first distance differs from the second distance, directing the second signal can include directing the second signal to represent a time-varying second view, with the second view being a portion of the first view and occupying a second area less than the first area. The location of the second area relative to the first area can be selected based at least on an amount by which the first and second distances differ.

DETAILED DESCRIPTION

The present disclosure describes methods and systems for providing an image in a moving vehicle representative of a view external to the vehicle. Many specific details of certain embodiments of the invention are set forth in the following description and in FIGS. 1–10B to provide a thorough understanding of these embodiments. One skilled in the art, however, will understand that the present invention may have additional embodiments, and that the invention may be practiced without several of the details described below.

Embodiments of the invention can provide people inside a vehicle with a simulated, time-varying view of the region outside the vehicle, in a manner that is consistent with the motion of the vehicle. In one embodiment, the vehicle can include a passenger aircraft having few or no passenger windows. For purposes of illustration, aspects of the system are described in the context of a blended wing body aircraft. In other embodiments, the system can be incorporated into aircraft having configurations, and/or vehicles other than aircraft.

Figure 1:
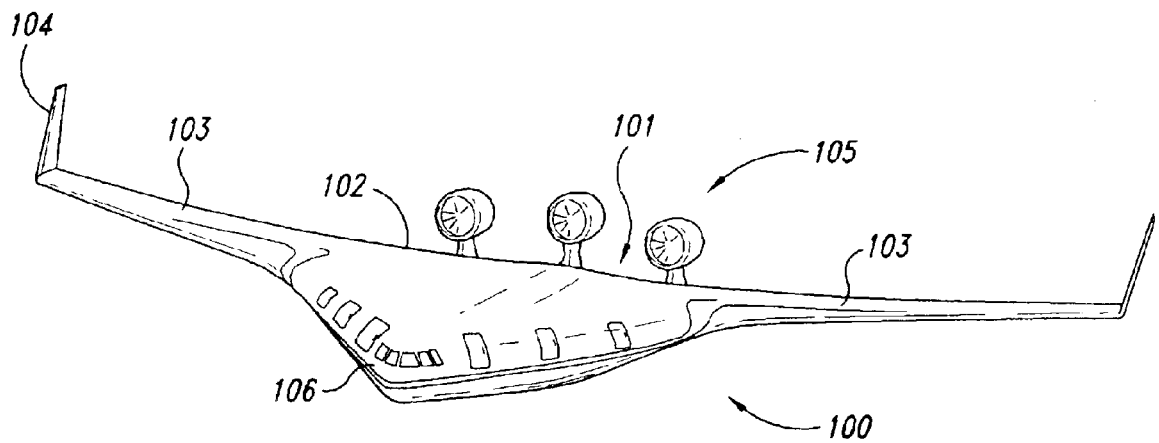
FIG. 1 is a partially schematic, front isometric illustration of an aircraft having a system for directing images of a view outside the aircraft to viewers within the aircraft in accordance with an embodiment of the invention.
Figure 2:
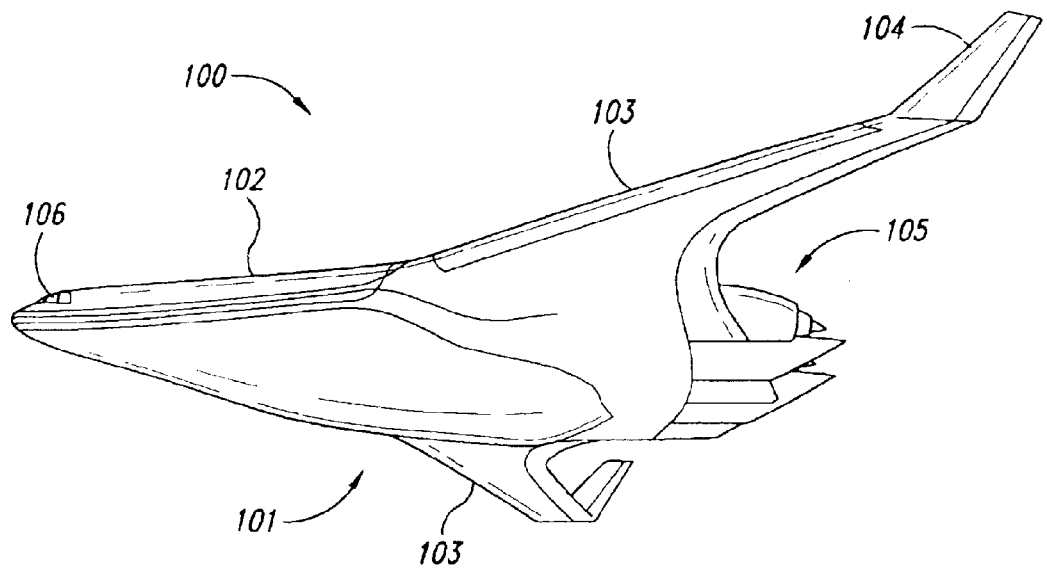
FIG. 2 is a partially schematic bottom isometric view of the aircraft shown in FIG. 1.

FIGS. 1 and 2 are partially schematic illustrations of an aircraft 100 having a blended wing body configuration in accordance with an embodiment of the invention. In one aspect of this embodiment, the aircraft 100 can include a blended wing body 101 having a central portion 102 for carrying a payload. Outboard portions 103 can extend laterally outwardly from the central portion 102. The aircraft 100 can include winglets 104 for lateral stability, and a propulsion system 105 for power. In one aspect of this embodiment, the propulsion system 105 can include three engines mounted above the upper surface of the blended wing body 101, and in other embodiments the propulsion system 105 can have other arrangements. In any of these embodiments, the central portion 102 can include a forward-facing flight deck 106 from which the aircraft is operated.

Figure 3:
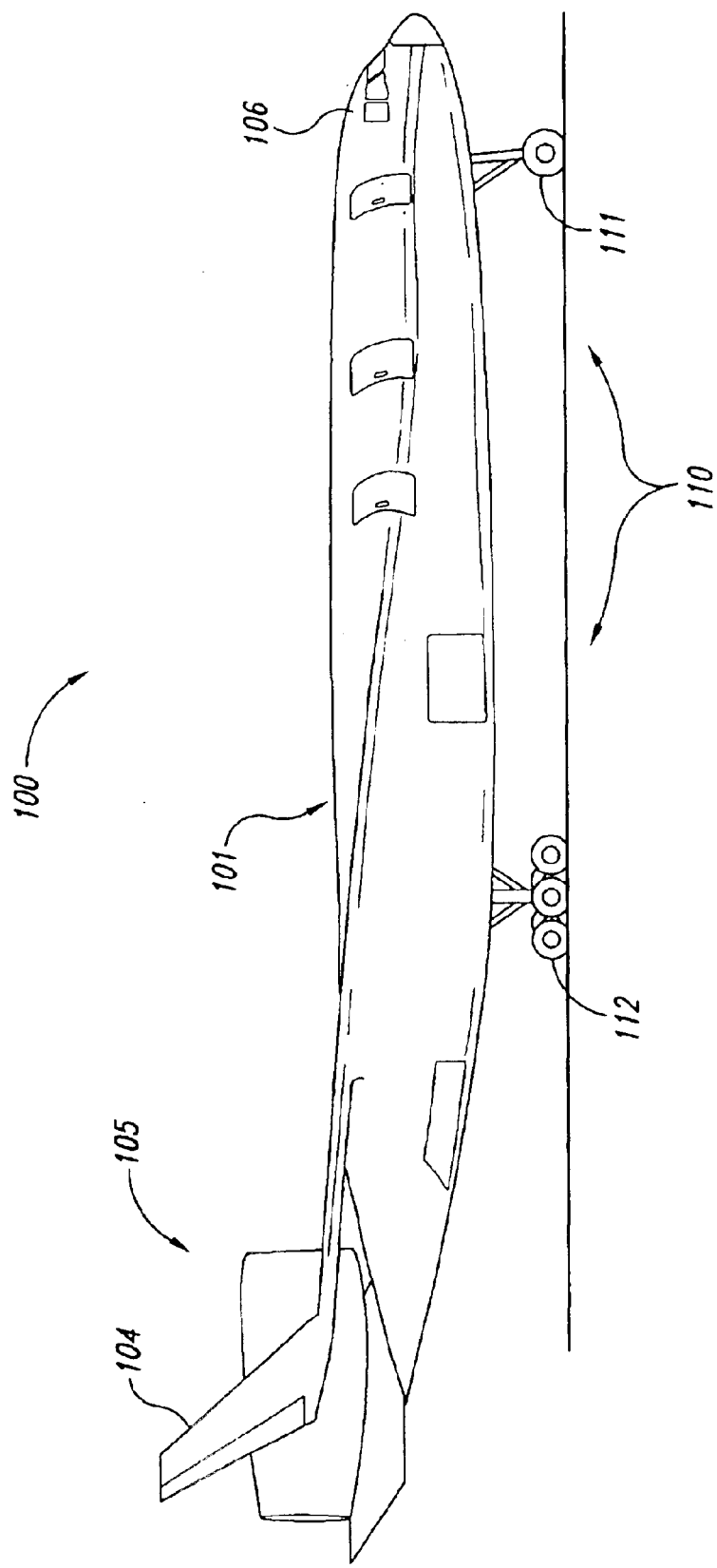
FIG. 3 is a partially schematic, side elevational view of the aircraft shown in FIG. 1.

FIG. 3 is a partially schematic, side elevational view of an embodiment of the aircraft 100 illustrating the blended wing body 101 supported on landing gear 110. The landing gear 110 can include a nose gear 111 and a plurality of main gears 112. In other embodiments, the aircraft 100 can have other landing gear configurations.

Figure 4:
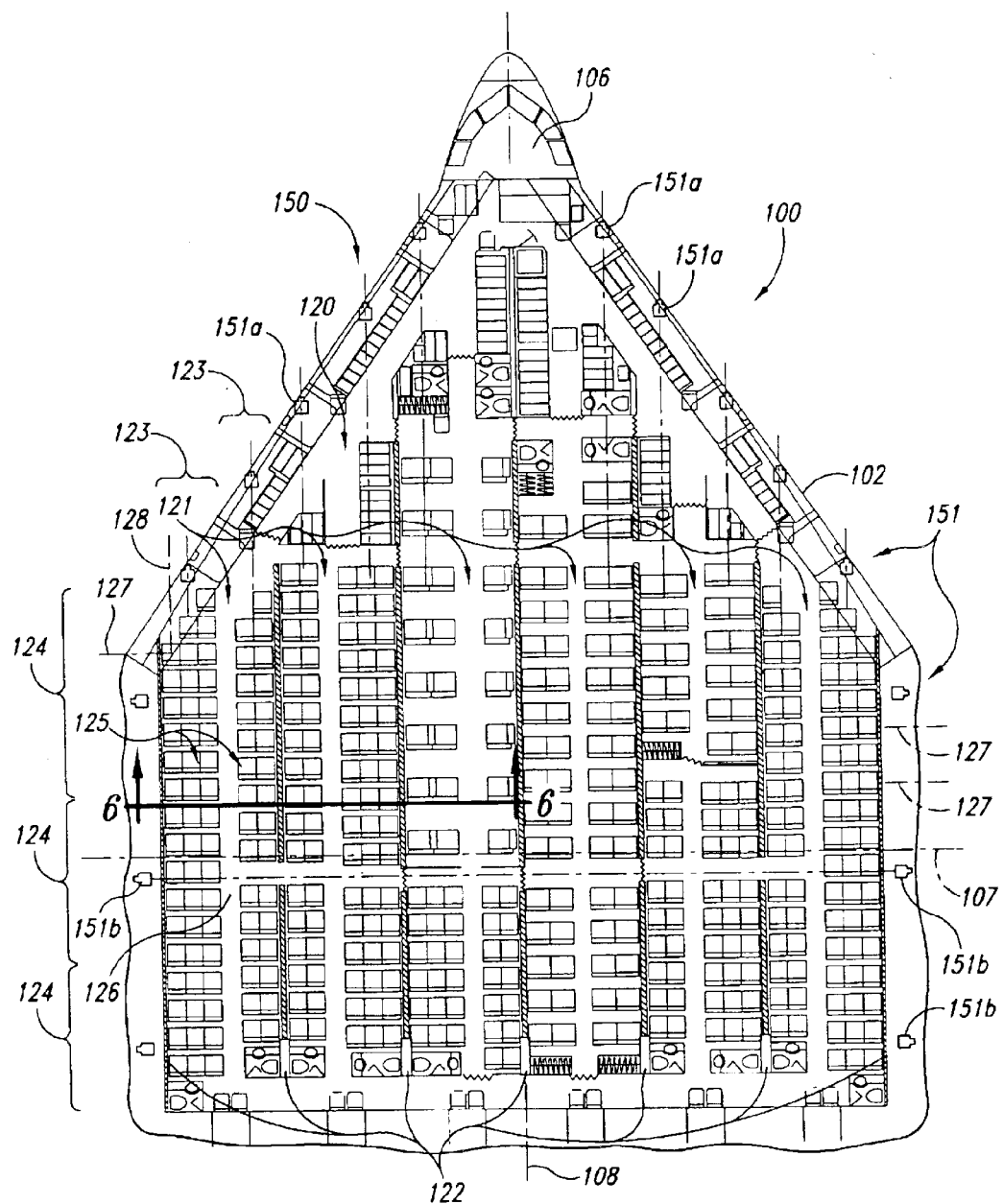
FIG. 4 is a partially schematic, top plan view of an interior of a portion of the aircraft shown in FIGS. 1–3, configured in accordance with an embodiment of the invention.

FIG. 4 is a partially schematic, top plan view of an interior portion of the aircraft 100, configured in accordance with an embodiment of the invention. In one aspect of this embodiment, the interior portion includes a passenger compartment 120 positioned aft of the flight deck 106. The passenger compartment 120 can be divided into a plurality of passenger bays 121 separated from each other by partitions 122. In a further aspect of this embodiment, each passenger bay 121 can be elongated in a direction generally parallel to a longitudinal or roll axis 108 of the aircraft 100. Each passenger bay 121 can house passenger seats 125 arranged in seat rows 127 (generally parallel to a pitch axis 107 of the aircraft 100) and seat columns 128 (generally parallel to the roll axis 108 of the aircraft 100). The seat columns 128 can be grouped into column groups 123 separated by the partitions 122 and/or by aisles 126, which are also aligned generally parallel to the longitudinal axis 108. The seat rows 127 can be grouped into row groups 124. In other embodiments, the interior of the aircraft 100 can have other passenger seating arrangements.

In any of the embodiments described above with reference to FIGS. 1–4, one characteristic of the aircraft 100 is that at least some of the seats 125 are not adjacent to a window and therefore passengers (not shown) in those seats do not have direct visual access to the region exterior to the aircraft 100. In fact, in at least one embodiment, the aircraft 100 can include few or no windows other than those at the flight deck 106. An advantage of a windowless (or reduced window) passenger compartment 120 is that it can allow for the efficient use of a relatively wide interior space, for example, the space provided by a blended wing body design. A further advantage is that eliminating or reducing the number of windows in the passenger compartment 120 can reduce the cost of manufacturing and/or maintaining the aircraft 100. However, the lack of windows may be uncomfortable for some passengers and may increase the likelihood that some passengers suffer from air sickness because they do not have access to visual cues that are consistent with the motion they feel. Embodiments of the invention described below include systems and methods for presenting to the passengers a series of images representative of the view external to the aircraft, in a manner that appears to move consistently with the motion the passenger feels.

In one embodiment, the aircraft 100 can include an image source 150 having several cameras 151 or other devices configured to receive images of the environment external to the aircraft 100 as the aircraft 100 moves. In one aspect of this embodiment, the image source 150 can include first cameras 151a positioned at varying distances from the roll axis 108 of the aircraft 100 and having focal lengths generally aligned with the roll axis 108. Each of the first cameras 151a can transmit a forward-looking image to passengers seated in a corresponding column group 123 of seats 125. In another embodiment, passengers seated in each seat column 128 (rather than in each column group 123) can have a dedicated first camera 151a from which they receive an image of the view external to the aircraft 100. In either embodiment, passengers seated relatively close to the roll axis 108 will view an image that moves relatively slowly and covers a relatively small arc as the aircraft rolls about the roll axis 108. Passengers seated further from the roll axis 108 will receive a view that moves more quickly and covers a larger arc.

In a further aspect of this embodiment, the image source 150 can also include second cameras 151b positioned at varying distances from the pitch axis 107 of the aircraft 100, and having focal lengths generally aligned with the pitch axis 107. In a manner generally similar to that described above, the second cameras 151b can transmit time-varying images to passengers in different rows 127 or row groups 124 to provide those passengers with side-looking views that move in a manner consistent with the movement the passenger feels as the aircraft rotates about the pitch axis 107.

Figure 5:
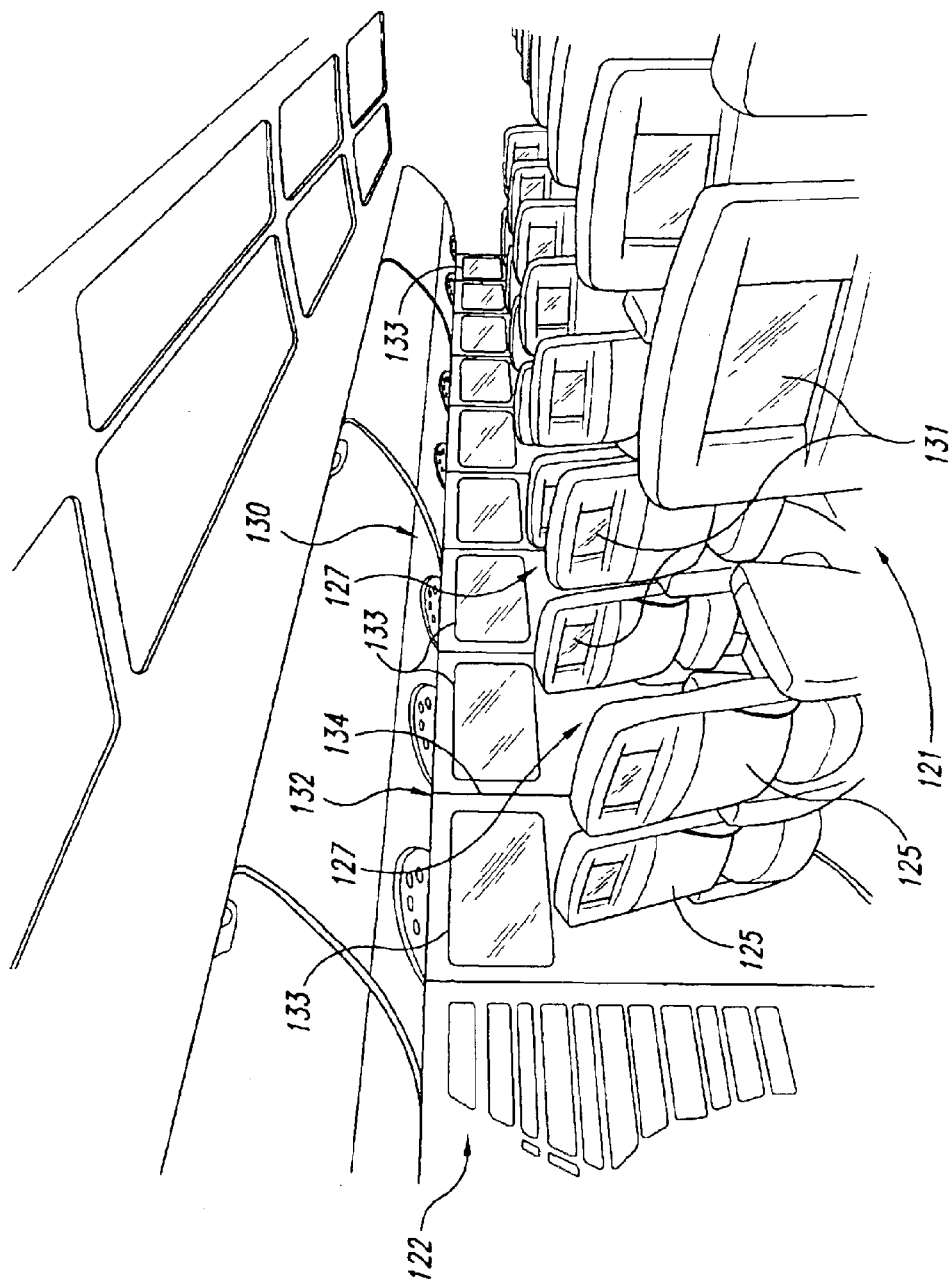
FIG. 5 is a partially schematic, forward-looking isometric illustration of the interior of a portion of an aircraft configured in accordance with an embodiment of the invention.

FIG. 5 is a partially schematic, forward-looking view of a passenger bay 121 configured in accordance with an embodiment of the invention. In one aspect of this embodiment, passengers at each seat 125 of the passenger bay 121 have visual access to a display system 130. The display system 130 can present to the passengers images received from the image source 150 described above with reference to FIG. 4. In a further aspect of this embodiment, the display system 130 can include a plurality of forward displays 131 positioned, for example, in the seat back of each seat 125. The display system 130 can also include a side display 132 positioned to the side of each seat 125, for example, along the partition 122 of the passenger bay 121. In still a further aspect of this embodiment, the side display 132 can include a plurality of display portions 133 separated by separators or partitions 134. The separators 134 can be positioned between each seat row 127 or between each row group 124 (FIG. 4), or the separators 134 can be eliminated.

In any of the foregoing embodiments, passengers seated within the passenger bay 121 can receive (from the forward displays 131) visual cues corresponding to a forward-looking view from the aircraft 100, and (from the side displays 132), visual cues corresponding to a side-looking view from the aircraft 100. With access to both these views, the passengers can receive visual cues that correspond to the motion they feel as the aircraft pitches and rolls, despite the absence of windows within the passenger bay 121. Accordingly, the passengers within the passenger bay 121 can be less susceptible to motion sickness. This result can be achieved in one embodiment by providing different passengers or groups of passengers with images from different cameras, with the cameras capturing images that move in a manner similar to the images the passengers would capture with their own eyes if they could see through the walls of the aircraft 100. In other embodiments, a single camera or other image source can be used to provide different images to different passengers or groups of passengers, as described in greater detail below with reference to FIGS. 6–9.

Figure 6:
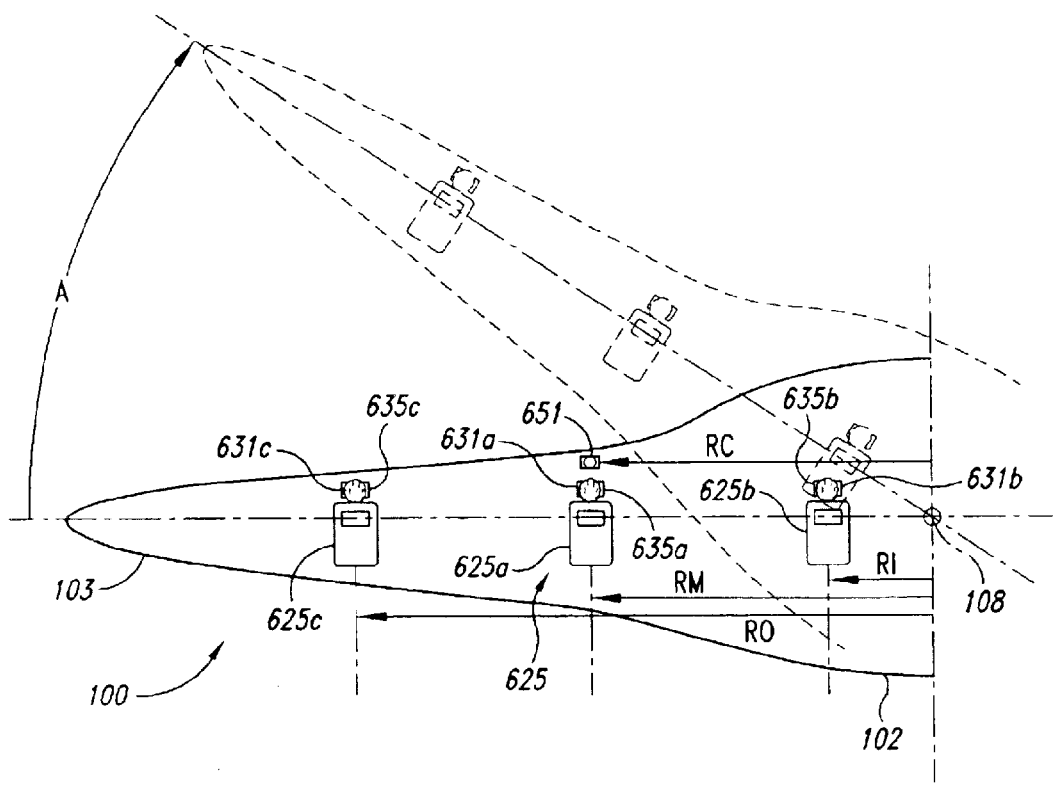
FIG. 6 is a partially schematic cross-sectional view of an aircraft configured in accordance with an embodiment of the invention, taken substantially along line 6—6 of FIG. 4.

FIG. 6 is a partially schematic, cross-sectional illustration of a left portion of the aircraft 100 taken substantially along line 6—6 of FIG. 4. In one aspect of this embodiment, the aircraft 100 can include a single forward-facing camera 651 positioned a distance or radius RC from the roll axis 108. In another aspect of this embodiment, another camera (not shown in FIG. 6) can be positioned at the right portion of the aircraft 100. In still another embodiment, a single camera can be axially aligned with the roll axis 108 instead of being positioned away from the roll axis 108.

Several representative seats 625 are also shown in FIG. 6, including a median seat 625a positioned a distance RM from the roll axis 108 and at least approximately aligned with the camera 651. An inboard seat 625b can be positioned a distance RI from the roll axis 108, and an outboard seat 625c can be positioned a distance RO from the roll axis 108. Corresponding median inboard and outboard forward displays 631a–631c, respectively, can be positioned before the passengers in seats 625a–625c, respectively. The median forward display 631a can present a median display image 635a, the inboard forward display 631b can present an inboard display image 635b, and the outboard forward display 631c can present an outboard display image 635c.

As the aircraft 100 rolls through a roll angle A, the passengers travel through arcs that vary in length depending upon the distance each passenger is from the roll axis 108. Passengers sitting close to the roll axis 108 would expect, if they could see through the front of the aircraft 100, to have their eyes sweep through a relatively short arc as the aircraft rolls through the roll angle A, and passengers positioned further from the roll axis 108 would expect their eyes to sweep through a relatively larger arc. As described below with reference to FIGS. 7A–9, embodiments of the invention can simulate this view from a single camera 651 or other image source.

Figure 7A:
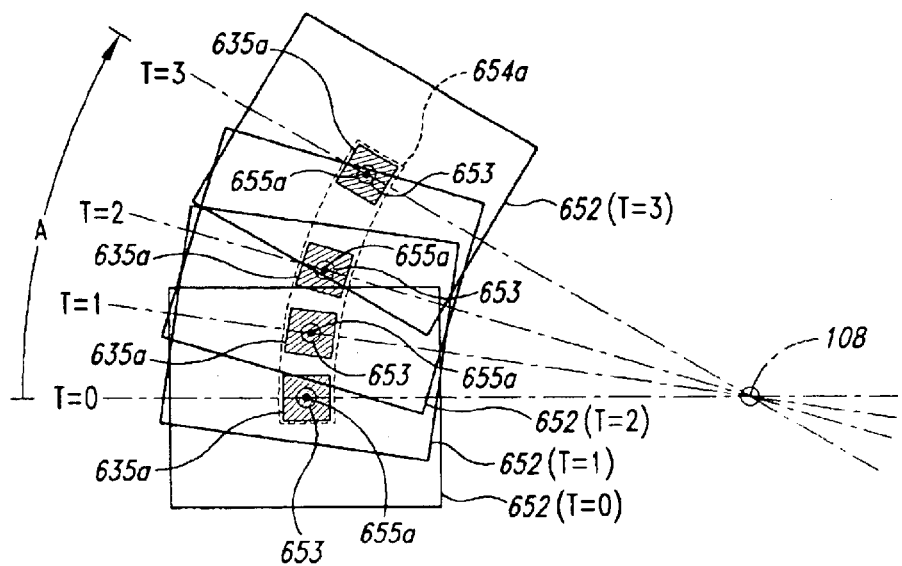
FIG. 7A is a partially schematic illustration of the movement of a camera field of view, upon which is superimposed the movement of a display portion view corresponding to a seat axially aligned with the camera in accordance with an embodiment of the invention.

FIG. 7A illustrates the roll axis 108 of the aircraft 100, together with a camera view field 652 having a view field centroid 653. The camera view field 652 corresponds to the field of view of the camera 651 (described above with reference to FIG. 6) at a representative distance in front of the camera 651. The camera view field 652 is shown simultaneously at four different time intervals (labeled T=0, T=1, T=2, and T=3). Each view field 652 corresponds to the view the camera 651 captures at a successive point in time as the aircraft 100 (FIG. 6) rolls through angle A. The median display image 635a presented to a passenger sitting in the median seat 631a (FIG. 6) is also shown at the same four time intervals (T=0, T=1, T=2, and T=3), superimposed on the corresponding camera view field 652. In one aspect of this embodiment, the median display image 635a is smaller than the camera view field 652 and subtends a smaller viewing angle than does the camera view field 652. Because the camera 651 and the median display image 635a are positioned at about the same distance from the roll axis 108, a median display centroid 655aa of the median display image 635a tracks the motion of the view field centroid 653 as the aircraft 100 (and the camera view field 652) rotate. As the aircraft 100 rolls, the median display image 635a sweeps out an envelope 654a.

Figure 7B:
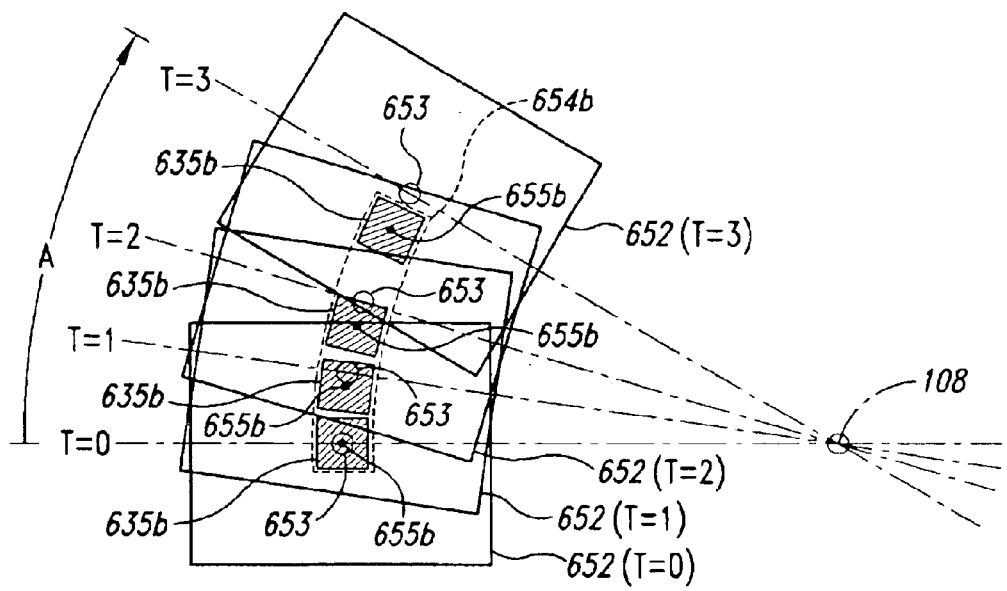
FIG. 7B is a partially schematic illustration of a moving camera field of view, upon which is superimposed the view at a display portion located proximate to a seat positioned axially inboard of the camera in accordance with another embodiment of the invention.

FIG. 7B is a schematic illustration of the camera view field 652 at times T=0, T=1, T=2 and T=3, upon which is superimposed the inboard display image 635b (at the same time intervals). The inboard display image 635b is displayed to a passenger sitting at the representative inboard seat 625b (FIG. 6) and has an inboard display centroid 655a. As the camera view field 652 sweeps through angle A, the inboard display centroid 655b, which is initially centered on the view field centroid 653, lags the motion of the view field centroid 653. Accordingly, an envelope 654b swept out by the motion of the inboard display image 635b is smaller than the envelope 654a described above with reference to FIG. 7A. This is consistent with the fact that a passenger seated inboard of the camera 651 (FIG. 6) and looking straight ahead, will experience a change in view field that is less than the change in the view field of the camera 651.

In a particular aspect of this embodiment, the degree to which the motion of the inboard display centroid 655b lags the motion of the view field centroid 653 is directly related to the amount by which the distance between the roll axis 108 and the camera 651 (i.e., RC shown in FIG. 6) differs from the distance between the roll axis 108 and the inboard seat 625b (i.e., RI shown in FIG. 6). In still a further aspect of this embodiment, the degree to which the motion of the inboard display centroid 655b lags the motion of the view field centroid 653 is proportional to RI divided by RC. Referring now to FIG. 6, this fraction is less than 1.0 for inboard seats. For seats 625a aligned with the camera 651, this fraction is RM divided by RC, which equals 1.0. For seats outboard of the camera 651, this fraction is RO divided by RC, which is greater than 1.0. Accordingly, the motion of the display images for seats outboard of the camera 651 can lead the motion of the view field centroid 653, as described below with reference to FIG. 7C.

Figure 7C:
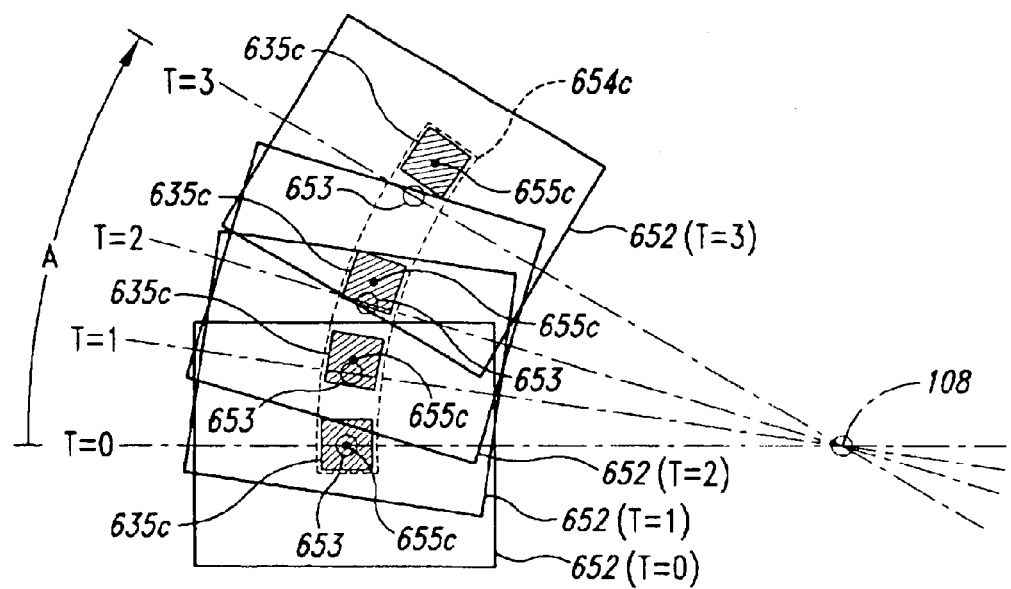
FIG. 7C is a partially schematic illustration of a moving camera field of view, upon which is superimposed the view at a display portion positioned proximate to a seat located axially outboard of the camera in accordance with another embodiment of the invention.

FIG. 7C is a schematic illustration of the camera view field 652 (at times T=0, T=1, T=2 and T=3), upon which is superimposed the outboard image 635c (also at times T=0, T=1, T=2 and T=3), as the aircraft 100 rotates about the roll axis 108 through angle A. As shown in FIG. 7C, the outboard image 635c sweeps out an envelope 654c. An outboard display centroid 655c leads the motion of the view field centroid 653. This motion is consistent with- the fact that a passenger seated outboard of the camera 651 (FIG. 6), and looking straight ahead will visually sweep out a greater area if he or she were able to see through the front of the aircraft 100, than would a passenger at the inboard seat 625b or the median seat 625a.

Referring now to FIGS. 6 and 7A–7C together, the camera view field 652 can be selected so that for the range of seats to which the camera 651 transmits image signals and for an expected range of aircraft rotation angles and angular velocities, the motion of the corresponding display images 635a–c will not pass out of the camera view field 652. For example, the camera view field 652 can be selected so that for the inboard-most seat 625b, the inboard display image 635b (FIG. 7B) will not fall below the lower limit of the camera view field 652 at the maximum roll angle. Similarly, the camera view field 652 can be selected so that for the outboard-most seat 625c, the outboard display image 635c (FIG. 7C) will not pass above the outer limit of the camera view field 652 at the maximum roll angle. For any display image that leads or lags the motion of the view field centroid 653, the amount of lead or lag will increase as the rotation of the aircraft 100 about the roll axis increases, will remain at a fixed distance from the centroid when the maximum roll angle is attained, and will realign with the view field centroid 653 when the aircraft 100 returns to a zero roll attitude.

Figure 8:
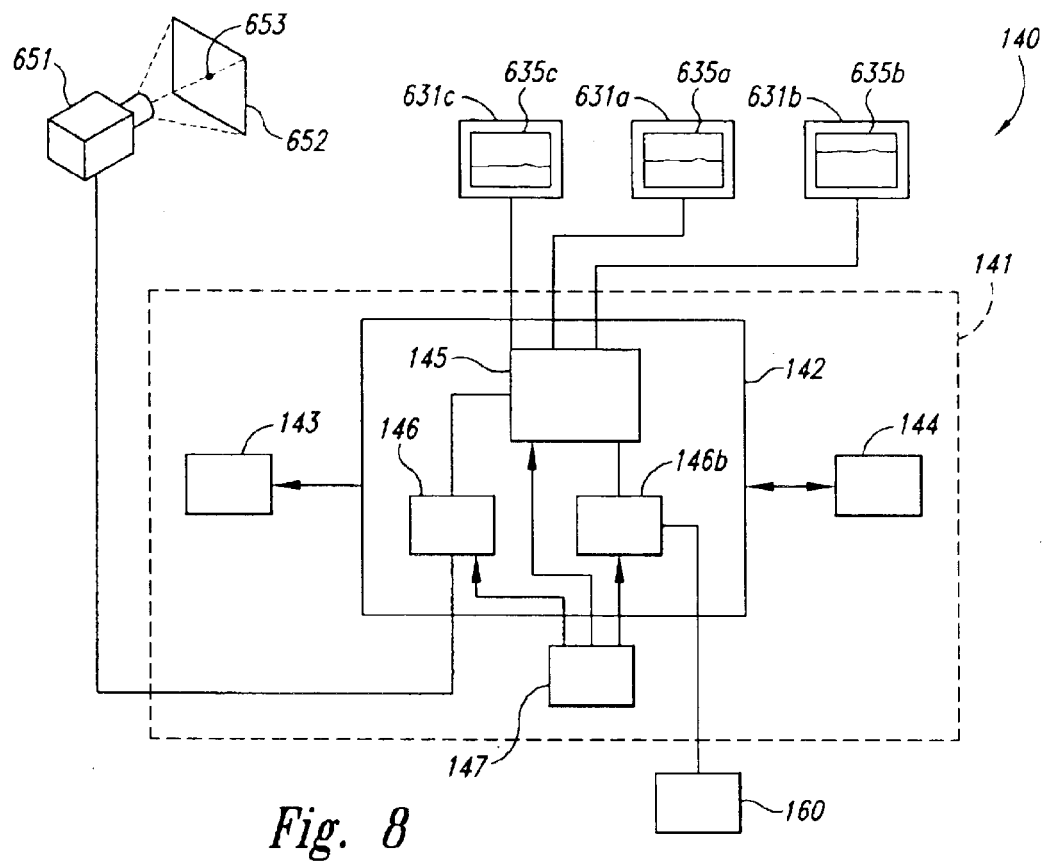
FIG. 8 is a schematic illustration of a system for presenting differing views to different displays in accordance with an embodiment of the invention.

FIG. 8 is a schematic illustration of a system 140 configured to receive images from the camera 651 or other image source, process the images, and transmit images to the forward displays 631a–c in a manner generally similar to that described above with reference to FIGS. 6–7C. In one aspect of this embodiment, the system 140 can include a computer 141 having a processor 142 configured to receive and process signals, a system display 143 configured to display diagnostics of the system 140, a system input/output portion 144 configured to receive or transmit external commands, and a memory 147 configured to store data. The processor 142 can include a first signal receiving portion 146a configured to receive time-varying signals from the camera 651. These signals can include digital images of the camera view field 652 described above with reference to FIGS. 7A–C. The processor 142 can further include a second signal receiving portion 146b configured to receive signals corresponding to the motion of the aircraft 100 (FIG. 6). For example, the second signal receiving portion 146b can be coupled to a motion sensor 160 (such as an inertial sensor) configured to detect motion of the aircraft about the roll axis 108 (FIG. 4) or the pitch axis 107 (FIG. 4). A signal processing portion 145 can process signals from the signal receiving portions 146 in a manner generally similar to that described above with reference to FIGS. 7A–C. Accordingly, the signal processing portion 145 can crop the camera view field 652 to correspond to the appropriate display images 635a–635c. The signal processing portion 145 can then direct appropriately corresponding time-varying signals to each of the forward displays 631a–631c. The motion of the display images 635a–635c can lead, lag or track the motion of the view field centroid 653 as the aircraft 100 rotates, in a manner generally similar to that described above.

In a particular embodiment, the camera 651 can transmit a stream of digital images that is stored or cached in the computer memory 147. Each forward display portion 631a–631c can have associated with it a register that represents the distance between it and the corresponding rotation axis, relative to the position of the camera 651 or other image source. The processing portion 145 can sample the digitally stored images and select the data bits corresponding to the display image 635 for the appropriate forward display 631. As the aircraft 100 rotates, the selected data bits can correspond to an image that lags, leads or tracks the motion of the centroid 653, depending on whether the display portion is inboard, outboard or aligned with the camera 651. When the aircraft 100 stops rotating, the selected data bits can correspond to an image that aligns with the view field centroid 653.

Figure 9:
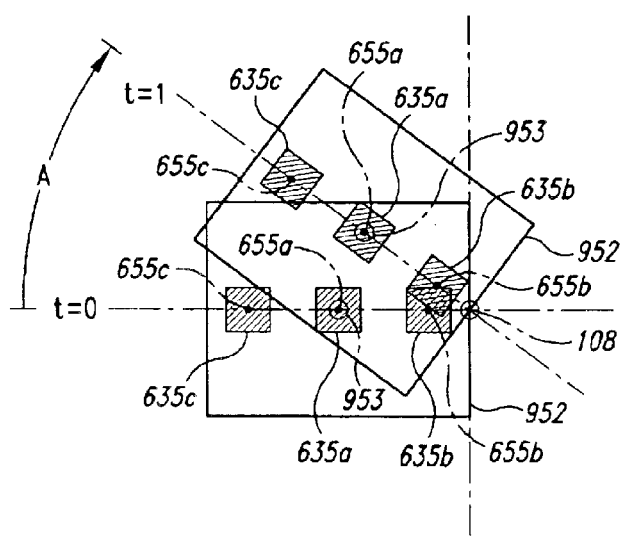
FIG. 9 is a partially schematic illustration of a moving camera field of view upon which is superimposed three display portion views in accordance with another embodiment of the invention.

FIG. 9 is a schematic illustration of a method in accordance with another embodiment of the invention in which an image received by the camera 651 (FIG. 6) or other image source can be manipulated to provide different images to passengers in different seats within the airplane 100 (FIG. 6). In one aspect of this embodiment, the camera 651 can present a camera view field 952 that moves through an angle A from time T=0 to time T=1. Median, inboard and outboard images 635a–c, respectively, having display centroids 655a–c respectively, can be extracted from the camera view field 952. In another aspect of this embodiment, the motions of the display centroids 655a–c do not lag or lead the motion of a view field centroid 953. Instead, the display images 635a–c (centered on the display centroids 655a–c) are extracted from different portions of the camera view field 952 based upon the distance between the roll axis 108 and the corresponding forward display 631a–c (FIG. 6) on which the display view fields 635a–c are presented. While this arrangement may not provide as accurate a simulation of the view forward of the aircraft 100 as that description above with reference to FIGS. 7A–7C, it can be simpler to implement. For example, this arrangement does not require information corresponding to the motion of the aircraft because the location of each display centroid 655a–c relative to the view field centroid 953 remains the same as the aircraft rolls about the roll axis 108. Accordingly, this arrangement can be implemented with a system generally similar to the system 140 described above with reference to FIG. 8, but without an input from the aircraft motion sensor 160 and without the second signal receiving portion 146b.

In other embodiments, the systems described above can be further simplified. For example, in one embodiment, the camera 651 can be eliminated and replaced with one or more stored images, such as a digital representation of a typical forward-looking view from an aircraft 100 flying over a typical terrain. As the aircraft 100 rotates, the system 140 can simulate the movement of the stored image through a path that simulates the path of the camera view field 652, described above with reference to FIGS. 7A–7C. The processor 145 can extract portions of these images that (a) lead or lag the motion of the view field centroid 653 (as discussed above with reference to FIGS. 7A–7C) or (b) have different but unchanging positions relation to the view field centroid 953 (as discussed above with reference to FIG. 9).

Figure 10A:
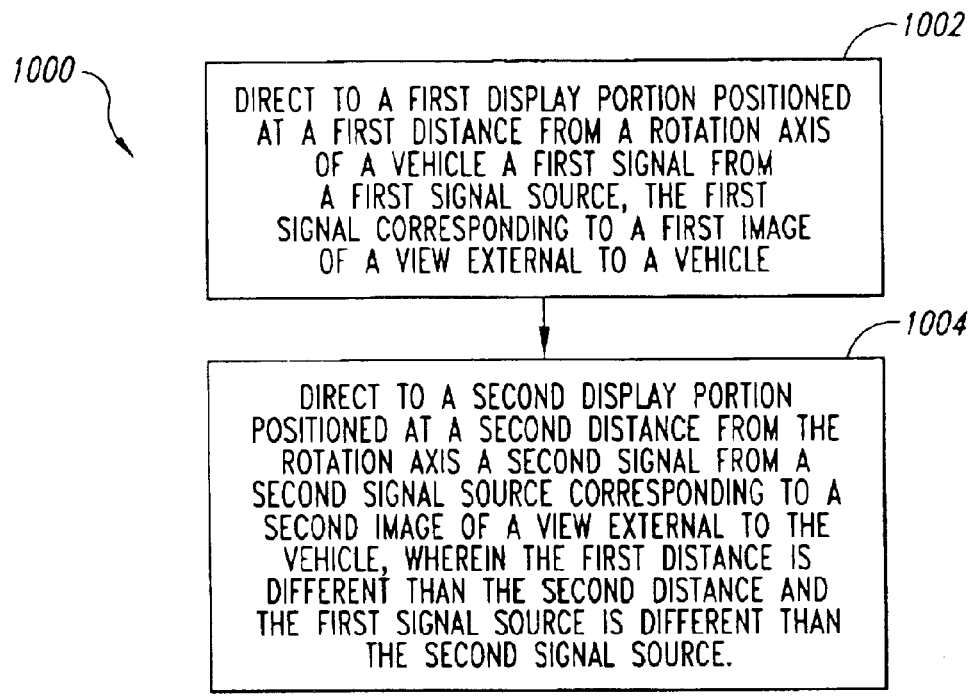
FIGS. 10A–10B are flow diagrams illustrating methods in accordance with embodiments of the invention.
Figure 10B:
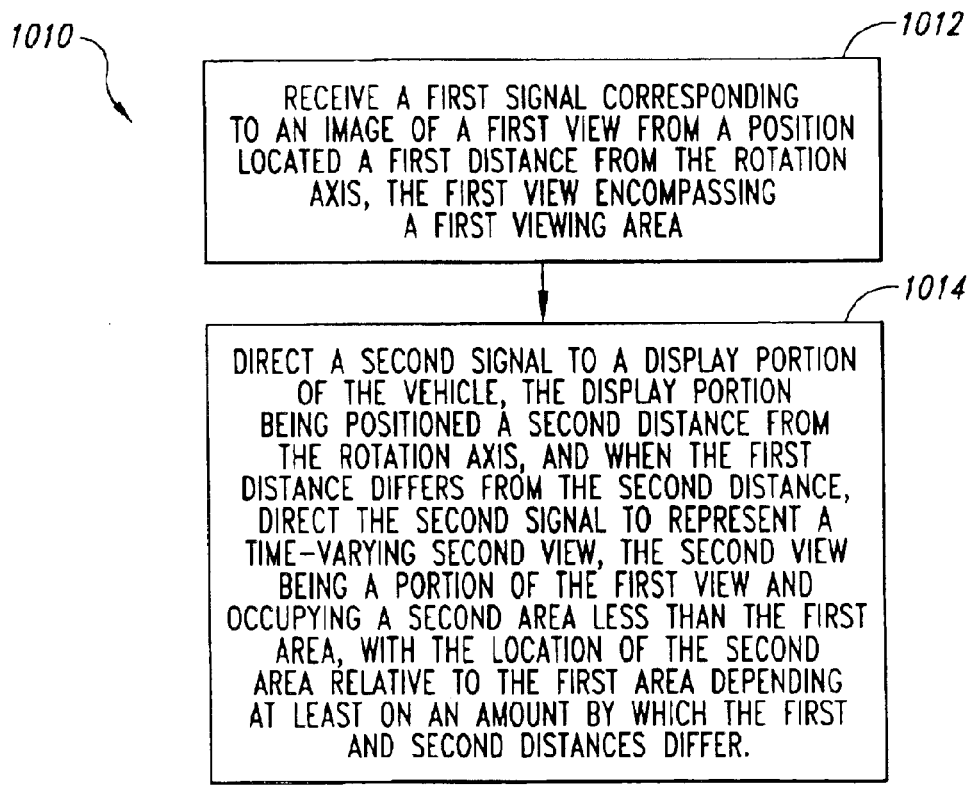

FIGS. 10A–10B are flow diagrams illustrating processes for displaying to different passengers within a moving vehicle, different images of a view external to the vehicle. FIG. 10A illustrates a process 1000 corresponding generally to an embodiment of the invention described above with reference to FIG. 4. Accordingly, the process 1000 can include directing to a first display portion positioned at a first distance from a rotation axis of a vehicle a first signal from a first signal source, the first signal corresponding to a first image of a view external to the vehicle (process portion 1002). In process portion 1004, the process 1000 includes directing to a second display portion positioned at a second distance from the rotation axis a second signal from a second signal source corresponding to a second image of a view external to the vehicle. The first distance is different than the second distance and the first signal source is different than the second signal source. For example, the first and second signal sources can correspond to any of the plurality of cameras 151 shown in FIG. 4, and the first and second distances can correspond to the varying distances from the roll axis 108 or the pitch axis 107.

Referring now to FIG. 10B, a process 1010 can correspond to an arrangement described above with reference to FIGS. 7A–7C or FIG. 9. In one aspect of this embodiment, the process 1010 can include receiving a first signal, corresponding to an image of a first view from a position located a first distance from the rotation axis with the first view encompassing a first viewing area (process portion 1012). In process portion 1014, the process 1010 includes directing a second signal to a display portion of the vehicle, with the display portion being positioned a second distance from the rotation axis. When the first distance differs from the second distance, directing the second signal can include directing the second signal to represent a time-varying second view, with the second view being a portion of the first view and occupying a second area less than the first area, and with the location of the second area relative to the first area depending at least on an amount by which the first and second distances differ.

In a further aspect of this embodiment (corresponding to an arrangement generally similar to that shown in FIGS. 7A–C), the location of the second area relative to the first area can change with time by an amount that is proportional to the distance between the display portion and the rotation axis divided by the distance between a corresponding viewpoint for the first signal and the rotation axis. In another embodiment, generally similar to that described above with reference to FIG. 9, the location of the second area relative to the first area is also proportional to the distance between the display portion and the rotation axis divided by the corresponding viewpoint for the first signal and the rotation axis, but is fixed with time. In either embodiment, the first signal can be received from a variety of sources, including a camera or a digitally or otherwise stored image.

An advantage of embodiments of the systems and methods described above is that they can simulate what passengers would actually see if they were able to have visual access to a region directly outside the aircraft or other vehicle. In particular, as the vehicle rotates about a rotation axis, passengers without direct visual access to the region outside the vehicle receive an image that simulates or represents a view that moves in a manner consistent with what the passenger feels. In one embodiment, the view can be provided by multiple cameras, with each camera directing its signal to a corresponding seat or group of seats. In other embodiments, the system can extract portions of images from one or more cameras, or from an image database, to provide different views to different passengers, in a manner that depends on the passenger's location relative to the rotation axis, and, optionally, the speed with which the vehicle rotates about the rotation axis.

From the foregoing, it will be appreciated that specific embodiments of the invention have been described herein for purposes of illustration, but that various modifications may be made without deviating from the spirit and scope of the invention. For example, in some embodiments the same or similar methods and systems as described above with reference to passenger seats and displays located at different distances from an aircraft roll axis can provide visual cues to passengers located at different distances from other axes, including the pitch axis 107. Accordingly, the invention is not limited except as by the appended claims.

I claim:

1. A system for presenting an image in a vehicle as the vehicle rotates about a rotation axis, the system comprising:

a signal receiving portion configured to receive a first signal corresponding to an image of a first view from a position located a first distance from the rotation axis, the first view encompassing a first viewing area; and a signal processing portion configured to direct to a display portion located a second distance from the rotation axis a time-varying second signal, the time-varying second signal representing a second view, the second view being a portion of the first view and occupying a second area less than the first area, wherein the location of the second area relative to the first area is selected based at least on an amount by which the first and second distances differ.

2. The system of claim 1 wherein the first and second views are of a region external to a vehicle.

3. The system of claim 1, further comprising an image source coupled to the signal processing portion to transmit the first time-varying signal.

4. The system of claim 1, further comprising a camera coupled to the signal processing portion to transmit the first time-varying signal.

5. The system of claim 1, further comprising the display portion.

6. The system of claim 1 wherein the signal receiving portion includes a first signal receiving portion and wherein the system further comprises a second signal receiving portion configured to receive a signal corresponding to a rotation of the vehicle about the rotation axis, further wherein the signal processing portion is configured to direct to the display portion the second time-varying signal with the location of the second area relative to the first area further selected based on the rotation of the vehicle about the rotation axis.

7. A system for presenting images corresponding to views external to a vehicle as the vehicle rotates about a rotation axis, the system comprising:

an image source positioned a first distance from the rotation axle and being configured to transmit a time-varying first signal as the vehicle rotates, the first signal representing a first view external to the vehicle, the first view encompassing a first viewing area;

a display portion positioned within the vehicle at a second distance from the rotation axis, the second distance being different than the first distance; and a processing portion coupled between the image source and the display portion, the processing portion being configured to receive the first signal from the image source and transmit a time-varying second signal to the display portion, the second signal representing a second view external to the vehicle, the second view being a portion of the first view and occupying a second area less than the first area, wherein the location of the second area relative to the first area depends at least in part on an amount by which the first and second distances differ.

8. The system of claim 7 wherein the first viewing area has a first centroid that rotates about the rotation axis at a first angular rate as the vehicle rotates about the rotation axis, and wherein the processing portion is configured to transmit the second signal representing the second view with the second area having a second centroid that rotates about the rotation axis at a second angular rate, the second angular rate being proportional to the first angular rate multiplied by the second distance and divided by the first distance.

9. The system of claim 7 wherein the wherein the first viewing area has a first centroid that rotates about the rotation axis at a first angular rate as the vehicle rotates about the rotation axis, and wherein the processing portion is configured to transmit the second signal representing the second view with the second area having a second centroid that rotates about the rotation axis at a second angular rate, the second angular rate being at least approximately the same as the first angular rate, the second centroid being spaced apart from the first centroid by a distance that is proportional to an amount by which the first and second distances differ.

10. The system of claim 7 wherein the vehicle includes an aircraft rotatable about a roll axis, and wherein the image source includes a camera mountable to the aircraft.

11. The system of claim 7 wherein the image source includes a camera having a focal axis and wherein the focal axis of the camera is oriented at least approximately parallel with the rotation axis.

12. A system for presenting an image in a vehicle as the vehicle rotates about a rotation axis, the system comprising:
   image receiving means for a first signal corresponding to an image of a first view from a position located a first distance from the rotation axis, the first view encompassing a first viewing area; and
   processing means for processing the first signal, the processing means being coupled to the image source means to receive the first signal and direct to a display portion located a second distance from the rotation axis a time-varying second signal, the time-varying second signal representing a second view, the second view being a portion of the first view and occupying a second area less than the first area, wherein the location of the second area relative to the first area is selected based at least on an amount by which the first and second distances differ.

13. The system of claim 12, further comprising the display portions.

14. The system of claim 12, further comprising image source means coupled to the image receiving means to transmit to the image receiving means the first signal.

15. An aircraft rotatable about a rotation axis, comprising:
   a fuselage portion;
   a wing portion depending from the fuselage portion;
   a propulsion system coupled to at least one of the fuselage portion and the wing portion;
   a signal receiving portion configured to receive a first signal corresponding to an image of a first view from a position located a first distance from the rotation axis, the first view encompassing a first viewing area; and
   a signal processing portion configured to direct to a display portion located a second distance from the rotation axis a time-varying second signal, the time-varying second signal representing a second view, the second view being a portion of the first view and occupying a second area less than the first area, wherein the location of the second area relative to the first area is selected based at least on an amount by which the first and second distances differ.

16. A method for presenting an image in a vehicle, comprising:
   while the vehicle rotates about a rotation axis:
   receiving a first signal corresponding to an Image of a first view from a position located a first distance from the rotation axis, the first view encompassing a first viewing area; and
   directing a second signal to a display portion of the vehicle, the display portion being positioned a second distance from the rotation axis;
   wherein when the first distance differs from the second distance, directing the second signal includes directing the second signal to represent a time-varying second view, the second view, being a portion of the first view and occupying a second area less than the first area, with the location of the second area relative to the first area being selected based at least on an amount by which the first and second distances differ.

17. The method of claim 16 wherein the second distance is less than the first distance, wherein the first area has a first centroid and wherein the second area has a second centroid, further wherein the first centroid rotates at a first rate about the rotation axis, still further wherein directing the second signal includes directing the second signal to form a second area having a second centroid that rotates at a second rate about the rotation axis, the second rate being less than the first rate.

18. The method of claim 16 further comprising receiving a third signal corresponding to a motion of the vehicle about the rotation axis.

19. The method of claim 16 wherein the second distance is less than the first distance, the first area has a first centroid and the second area has a second centroid, further wherein directing the second signal includes directing the second signal to form a second area having the second centroid positioned closer than the first centroid to the rotation axis.

20. The method of claim 16 wherein the first area has a first centroid and the second area has a second centroid, further wherein the first centroid rotates at a first rate about the rotation axis, still further wherein directing the second signal includes directing the second signal to form an image having a second area with a second centroid that rotates at a second rate about the rotation axis, the second rate being proportional to the second distance divided by the first distance.

21. The method of claim 16 wherein the first viewing area subtends a first viewing angle and wherein the second viewing area subtends a second viewing angle less than the first viewing angle.

22. The method of claim 16 wherein the vehicle includes an aircraft having a longitudinal roll axis and wherein the rotation axis is at least approximately the same as the roll axis.

* * * * *

UNITED STATES PATENT AND TRADEMARK OFFICE
CERTIFICATE OF CORRECTION

PATENT NO. : 7,046,259 B2 Page 1 of 1
APPLICATION NO. : 10/427429
DATED : May 16, 2006
INVENTOR(S) : Orin L. Humphries It is certified that error appears in the above-identified patent and that said Letters Patent is hereby corrected as shown below:

On title Page (item 56)
References Cited, Please insert http://www.tvphotography.com/fleetweek.htm, Called C-2 (4 pgs);

Column 10
Line 48, "axle" should be --axis--;

Column 12
Line 10, "Image" should be --image--;
Line 59, "roil" should be --roll--;

Signed and Sealed this

Fifteenth Day of August, 2006

JON W. DUDAS
*Director of the United States Patent and Trademark Office*